US011012659B2

(12) United States Patent
Mukherjee et al.

(10) Patent No.: US 11,012,659 B2
(45) Date of Patent: May 18, 2021

(54) INTELLIGENT ILLUMINATION AND SOUND CONTROL IN AN INTERNET OF THINGS (IOT) COMPUTING ENVIRONMENT

(71) Applicant: INTERNATIONAL BUSINESS MACHINES CORPORATION, Armonk, NY (US)

(72) Inventors: Maharaj Mukherjee, Poughkeepsie, NY (US); Shikhar Kwatra, Morrisville, NC (US); Komminist Weldemariam, Nairobi (KE); Sarbajit K. Rakshit, Kolkata (IN)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 77 days.

(21) Appl. No.: 16/057,683

(22) Filed: Aug. 7, 2018

(65) Prior Publication Data

US 2020/0053312 A1   Feb. 13, 2020

(51) Int. Cl.
*H04N 5/57* (2006.01)
*G05B 13/02* (2006.01)
*A61B 5/00* (2006.01)
*H04N 5/60* (2006.01)
*H05B 47/105* (2020.01)
*H05B 47/175* (2020.01)

(52) U.S. Cl.
CPC ............ *H04N 5/57* (2013.01); *A61B 5/7275* (2013.01); *G05B 13/026* (2013.01); *G05B 13/0265* (2013.01); *H04N 5/60* (2013.01); *H05B 47/105* (2020.01); *H05B 47/175* (2020.01)

(58) Field of Classification Search
CPC .......... H04N 5/57; H04N 5/60; G05B 13/026; G05B 13/0265; H05B 37/0227; H05B 37/0245
USPC ............................................ 348/460; 725/10
See application file for complete search history.

(56) References Cited

U.S. PATENT DOCUMENTS

| 8,854,390 | B2 | 10/2014 | Mineo et al. |
| 9,245,497 | B2* | 1/2016 | Pais ................... G06K 9/00281 |
| 10,192,473 | B2* | 1/2019 | Min ......................... G06T 5/40 |
| 10,212,494 | B1* | 2/2019 | Struhsaker .............. H04W 4/80 |
| 2006/0062424 | A1 | 3/2006 | Diederiks et al. |
| 2010/0107184 | A1* | 4/2010 | Shintani ............. H04N 21/4436 725/10 |
| 2010/0265414 | A1 | 10/2010 | Nieuwlands |

(Continued)

*Primary Examiner* — Jefferey F Harold
*Assistant Examiner* — Omer Khalid
(74) *Attorney, Agent, or Firm* — Griffiths & Seaton PLLC

(57) ABSTRACT

Embodiments for implementing intelligent illumination and sound characteristics control in an Internet of Things (IoT) computing environment by a processor. An intensity and quality of an illumination and sound characteristics of displayed media content in an IoT computing environment may be monitored and analyzed. A risk factor of one or more users may be estimated for both current settings and a predicted adjustment of the illumination and sound characteristics associated with displayed media content according to the analyzing. The illumination, the sound characteristics, or combination thereof of the displayed media content may be adjusted upon determining the risk factor for the one or more users is above a selected threshold.

20 Claims, 6 Drawing Sheets

(56) References Cited

U.S. PATENT DOCUMENTS

2015/0326570 A1* 11/2015 Publicover .............. G06F 3/017
726/4

* cited by examiner

INTELLIGENT ILLUMINATION AND SOUND CONTROL IN AN INTERNET OF THINGS (IOT) COMPUTING ENVIRONMENT

BACKGROUND OF THE INVENTION

Field of the Invention

The present invention relates in general to computing systems, and more particularly, to various embodiments for intelligent illumination and sound control in an Internet of Things (IoT) computing environment using a computing processor.

Description of the Related Art

In today's society, consumers, business persons, educators, and others use various computing network systems with increasing frequency in a variety of settings. The advent of computers and networking technologies have made possible the increase in the quality of life while enhancing day-to-day activities. Computing systems can include an Internet of Things (IoT), which is the interconnection of computing devices scattered across the globe using the existing Internet infrastructure. IoT devices may be embedded in a variety of physical devices or products.

SUMMARY OF THE INVENTION

Various embodiments for implementing intelligent illumination and sound characteristics control in an Internet of Things (IoT) computing environment by a processor, are provided. In one embodiment, by way of example only, a method for implementing intelligent illumination and sound characteristics of an entertainment system in an Internet of Things (IoT) computing environment, again by a processor, is provided. An intensity and quality of an illumination and sound characteristics of displayed media content in an IoT computing environment may be monitored and analyzed. A risk factor of one or more users may be estimated for both current settings and a predicted adjustment of the illumination and sound characteristics associated with displayed media content according to the analyzing. The illumination, the sound characteristics, or combination thereof of the displayed media content may be adjusted upon determining the risk factor for the one or more users is above a selected threshold.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which.

DETAILED DESCRIPTION OF THE DRAWINGS

Figure 1:
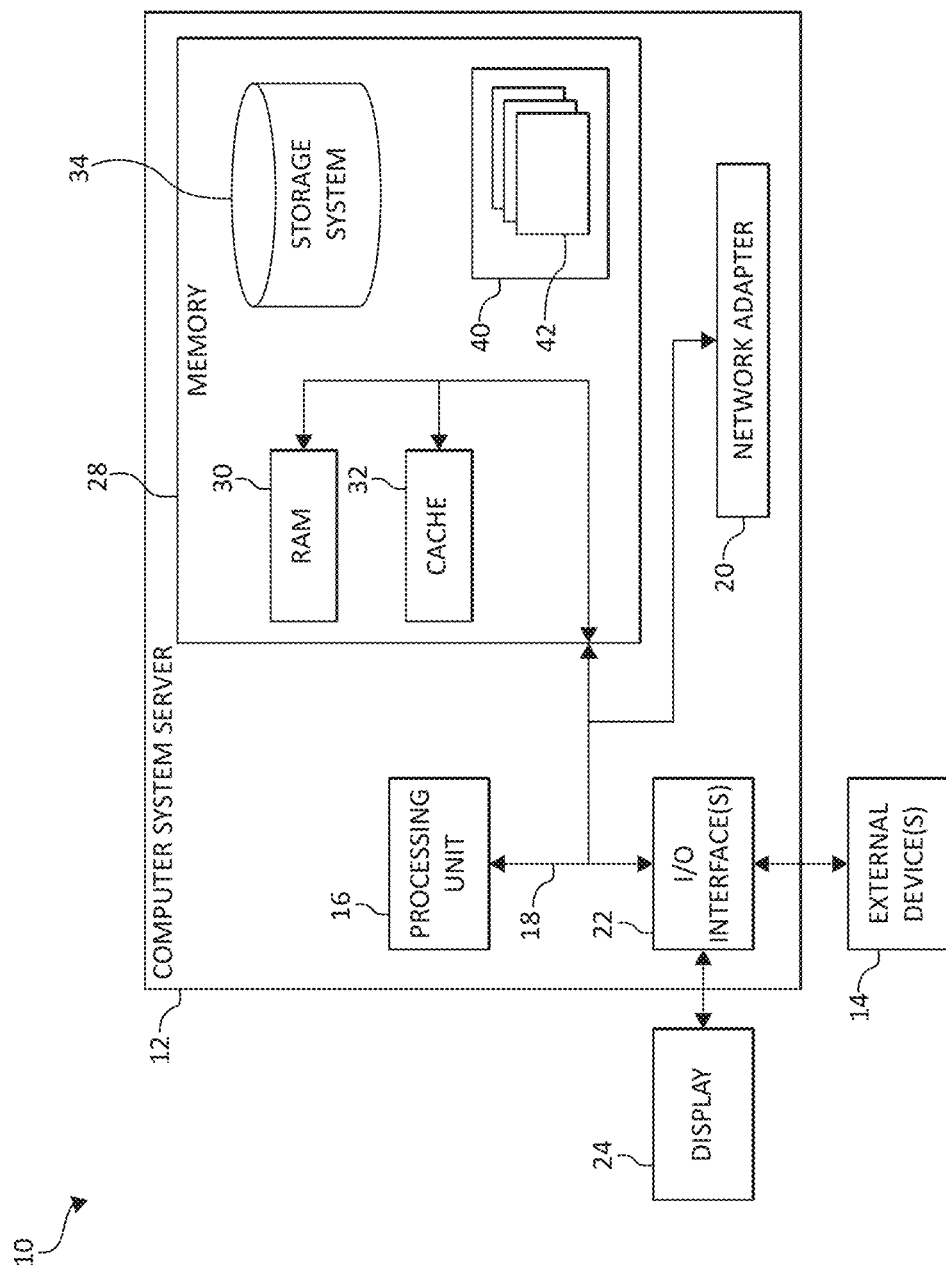
FIG. 1 is a block diagram depicting an exemplary cloud computing node according to an embodiment of the present invention.

As a preliminary matter, computing systems may include large scale computing called "cloud computing," in which resources may interact and/or be accessed via a communications system, such as a computer network. Resources may be software-rendered simulations and/or emulations of computing devices, storage devices, applications, and/or other computer-related devices and/or services run on one or more computing devices, such as a server. For example, a plurality of servers may communicate and/or share information that may expand and/or contract across servers depending on an amount of processing power, storage space, and/or other computing resources needed to accomplish requested tasks. The word "cloud" alludes to the cloud-shaped appearance of a diagram of interconnectivity between computing devices, computer networks, and/or other computer related devices that interact in such an arrangement.

The Internet of Things (IoT) is an emerging concept of computing devices that may be embedded in objects, especially appliances, and connected through a network. An IoT network may include one or more IoT devices or "smart devices", which are physical objects such as appliances with computing devices embedded therein. Examples of network-enabled appliances or devices may include computers, smartphones, laptops, wearable devices, sensor devices, voice-activated devices, face-activated devices, digital assistants, home appliances, audio systems, televisions, security cameras, security sensors, among countless other examples. Such IoT computing systems may be employed in a variety of settings.

For example, while one or more viewers are engaged in watching media content (e.g., a movie) in an entertainment system (e.g., a home theater system), the illumination and sound characteristics of the entertainment system significantly impacts the overall quality and enjoyment of a viewer's experience. For instance, reducing the amount lighting in a room may captivate the viewers' attention, increase the intensity of one or more scenes, and increase the user's excitement and enjoyment of the displayed media content. Furthermore, if the lighting in a room of the entertainment system is further reduced, then the level of brightness of a screen of a media display device (e.g., a television) should be reduced, along with the color contrast to eliminate any sort of viewer discomfort. Even while watching the media display device, the level of illumination in the room of the entertainment system (including one or more associated rooms, hallways, or corridors) may depend on various factors. For example, if young children are present in or near the entertainment system room, the reduced lightning may cause a negative reaction (e.g., becoming scared and afraid). Furthermore, the type of media content being displayed, may contain inappropriate content for visual consumption by the age-dependent viewers. Thus, one or more corrective and appropriate actions may be taken via a predictive or reactive approach to avoid the inappropriate content and/or complete darkness, which may be the source of fear or anxiety for the age dependent viewers.

Additionally, if another person is present in or near the entertainment system room, and suffers visual discomfort due to the reduced lightning, watching the media display device from the room with reduced lighting may further complicate a health and/or emotional state of the user (e.g., increased visual discomfort leading to possible headaches). In another scenario, the type of media content (e.g., video/gaming content) is an additional characteristic or parameter that may impact the health state, emotional state, or other biomedical condition of the viewer of the media content, particularly when combined with decreasing the illumination/lighting of surrounding the entertainment system room. For example, media content (e.g., video/gaming content) creating a spike in adrenaline levels may negatively impact a person suffering various cardiac irregularities thereby exposing the person to increased risks for cardiac arrest or additional irregularities.

Accordingly, the mechanisms of the illustrated embodiments provide for predictive adjustment and control of lighting/illumination and sound characteristics associated with displayed media in an entertainment system (e.g., a home theater setting) based on contextual analysis and risk levels of the one or more users.

In one aspect, an intensity and quality of the illumination and sound of displayed media content (e.g., movies, television programs, video games, audio, etc.) in an entertainment system (e.g., a home theater setting) may be monitored. One or more risk factors (e.g., health risk, comfort, eye strain, fatigue, blurry vision, fear, or other biological or emotional characteristics) of a viewer and/or a group of viewers of displayed content may be estimated with respect to both current and predicted illumination and sound intensity and quality using the monitored intensity and quality of illumination and sound. The intensity and quality of both the illumination and sound may be controlled and/or adjusted upon determining the risk level to one or more users is above a threshold level for the estimated risk factors.

In an additional aspect, an intensity and quality of the illumination and sound characteristics of displayed media content in an IoT computing environment may be monitored and analyzed. A risk factor of one or more users may be estimated for both current settings and a predicted adjustment of the illumination and sound characteristics associated with displayed media content according to the analyzing. The illumination, the sound characteristics, or combination thereof of the displayed media content may be adjusted upon determining the risk factor for the one or more users is above a selected threshold.

As used herein, so-called "appropriateness" of illumination and sound characteristic settings, such as a levels of lighting/illumination and sound characteristic settings, may be subjective and context dependent. For example, one solution for an appropriate level of illumination and sound characteristic settings may be interpreted and evaluated to be either satisfactory or unsatisfactory depending on the user profile of each user. Accordingly, the so-called "appropriateness" of a particular level of lighting/illumination and sound characteristic settings in an entertainment system may depend greatly upon contextual factors, such as a user profile, environmental factors, age/maturity levels, biometric data, a health profile, emotional data, and other contextual factors. A deeper, cognitive analysis of the user and levels of the illumination and sound characteristic settings may be provided to further understand the user and/or interpret the appropriate level of satisfaction.

It should be noted as described herein, the term "cognitive" (or "cognition") may be relating to, being, or involving conscious intellectual activity such as, for example, thinking, reasoning, or remembering, that may be performed using a machine learning. In an additional aspect, cognitive or "cognition may be the mental process of knowing, including aspects such as awareness, perception, reasoning and judgment. A machine learning system may use artificial reasoning to interpret data from one or more data sources (e.g., sensor based devices or other computing systems) and learn topics, concepts, and/or processes that may be determined and/or derived by machine learning.

In an additional aspect, cognitive or "cognition" may refer to a mental action or process of acquiring knowledge and understanding through thought, experience, and one or more senses using machine learning (which may include using sensor based devices or other computing systems that include audio or video devices). Cognitive may also refer to identifying patterns of behavior, leading to a "learning" of one or more events, operations, or processes. Thus, the cognitive model may, over time, develop semantic labels to apply to observed behavior and use a knowledge domain or ontology to store the learned observed behavior. In one embodiment, the system provides for progressive levels of complexity in what may be learned from the one or more events, operations, or processes.

In additional aspect, the term cognitive may refer to a cognitive system. The cognitive system may be a specialized computer system, or set of computer systems, configured with hardware and/or software logic (in combination with hardware logic upon which the software executes) to emulate human cognitive functions. These cognitive systems apply human-like characteristics to convey and manipulate ideas which, when combined with the inherent strengths of digital computing, can solve problems with a high degree of accuracy (e.g., within a defined percentage range or above an accuracy threshold) and resilience on a large scale. A cognitive system may perform one or more computer-implemented cognitive operations that approximate a human thought process while enabling a user or a computing system to interact in a more natural manner. A cognitive system may comprise artificial intelligence logic, such as natural language processing (NLP) based logic, for example, and machine learning logic, which may be provided as specialized hardware, software executed on hardware, or any combination of specialized hardware and software executed on hardware. The logic of the cognitive system may implement the cognitive operation(s), examples of which include, but are not limited to, question answering, identification of related concepts within different portions of content in a corpus, and intelligent search algorithms, such as Internet web page searches.

In general, such cognitive systems are able to perform the following functions: 1) Navigate the complexities of human language and understanding; 2) Ingest and process vast amounts of structured and unstructured data; 3) Generate and evaluate hypotheses; 4) Weigh and evaluate responses that are based only on relevant evidence; 5) Provide situation-specific advice, insights, estimations, determinations, evaluations, calculations, and guidance; 6) Improve knowledge and learn with each iteration and interaction through machine learning processes; 7) Enable decision making at the point of impact (contextual guidance); 8) Scale in proportion to a task, process, or operation; 9) Extend and magnify human expertise and cognition; 10) Identify resonating, human-like attributes and traits from natural language; 11) Deduce various language specific or agnostic attributes from natural language; 12) Memorize and recall relevant data points (images, text, voice) (e.g., a high degree of relevant recollection from data points (images, text, voice) (memorization and recall)); and/or 13) Predict and sense with situational awareness operations that mimic human cognition based on experiences.

It is understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities, but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 may include at least one program product having a set (e.g., at least one) of program modules that are configured to carry out the functions of embodiments of the invention.

Program/utility 40, having a set (at least one) of program modules 42, may be stored in memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples include, but are not limited to: microcode, device drivers, redundant processing units, external disk drive arrays, RAID systems, tape drives, and data archival storage systems, etc.

Figure 2:
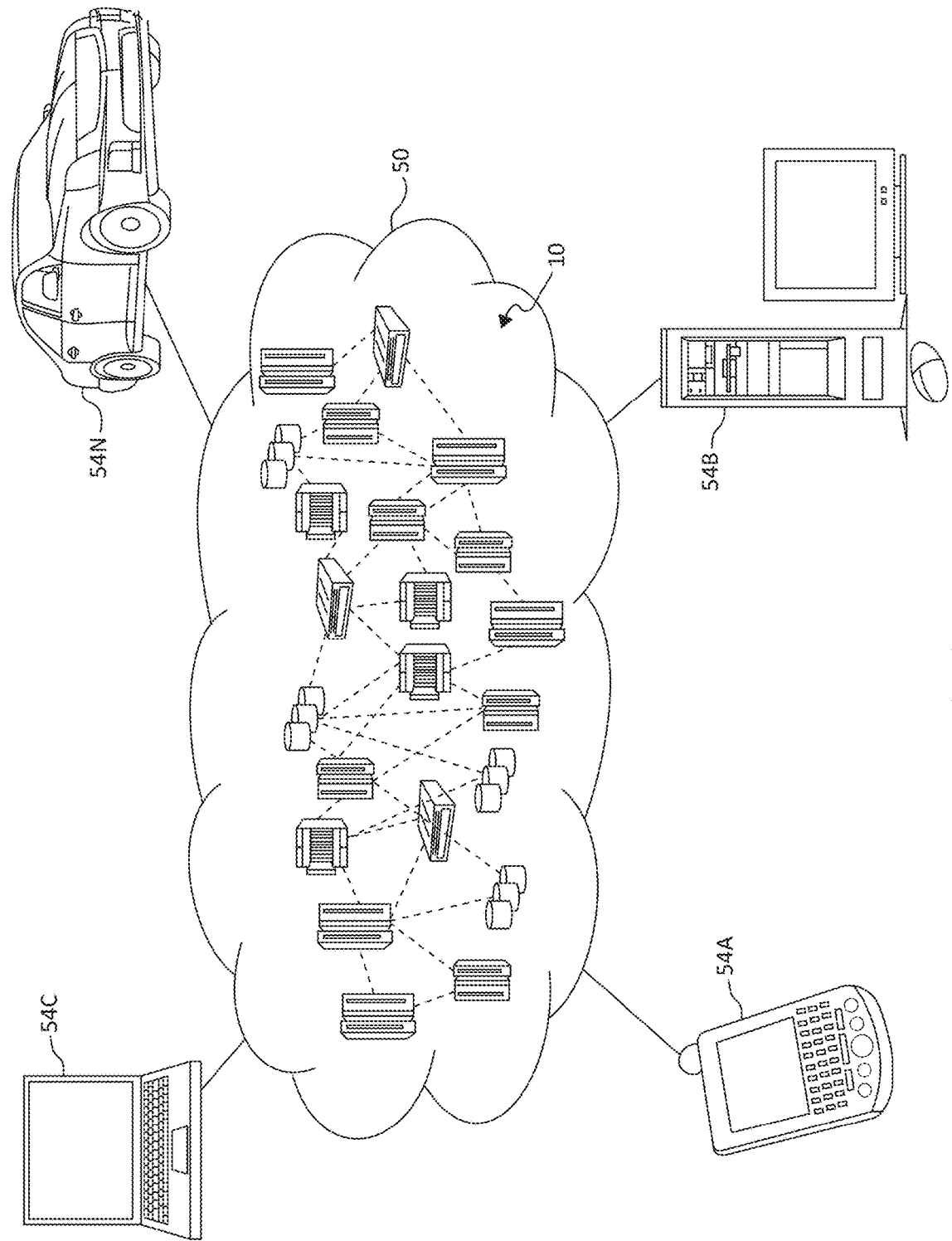
FIG. 2 is an additional block diagram depicting an exemplary cloud computing environment according to an embodiment of the present invention.

Referring now to FIG. 2, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
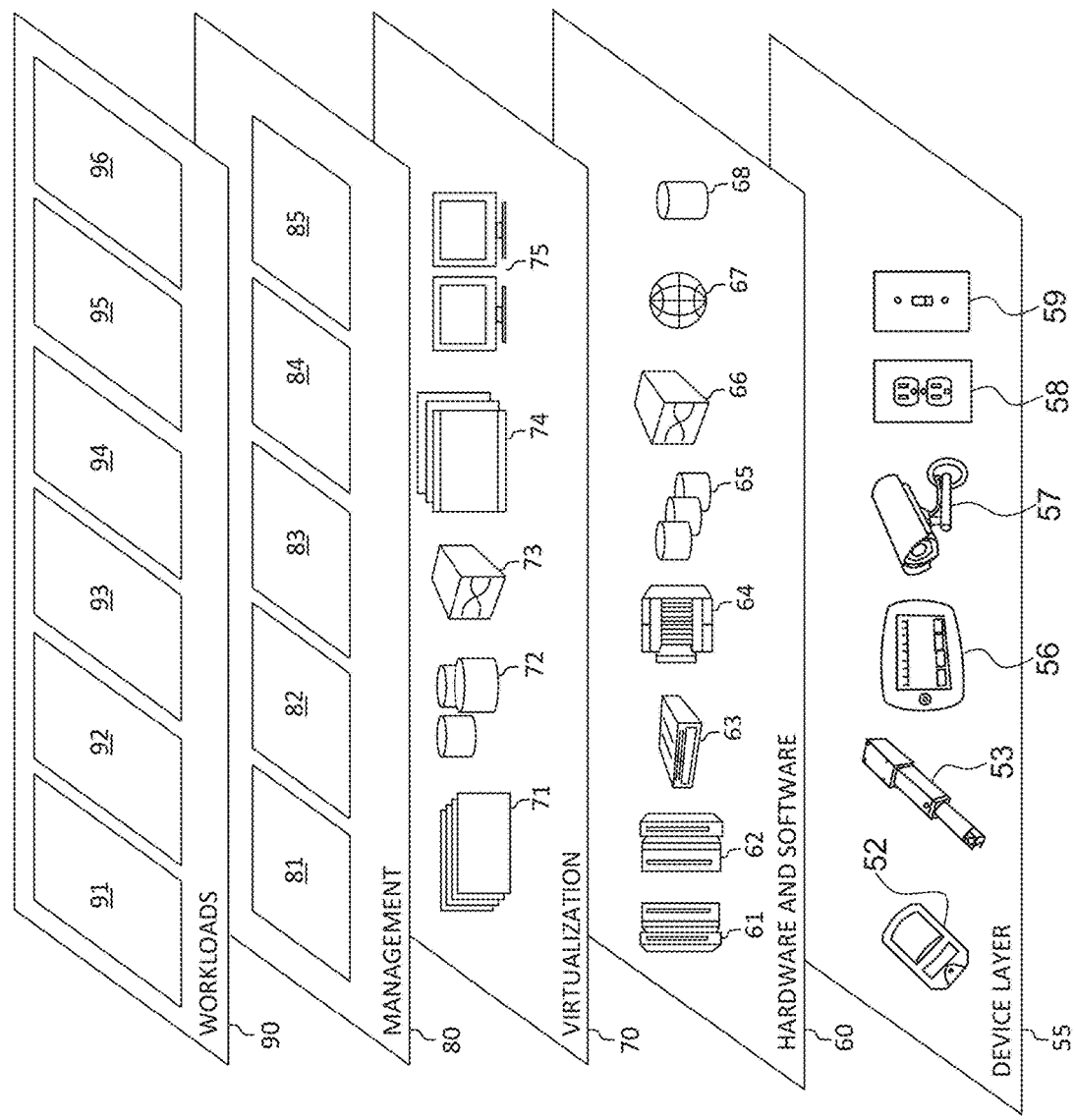
FIG. 3 is an additional block diagram depicting abstraction model layers according to an embodiment of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Device layer 55 includes physical and/or virtual devices, embedded with and/or standalone electronics, sensors, actuators, and other objects to perform various tasks in a cloud computing environment 50. Each of the devices in the device layer 55 incorporates networking capability to other functional abstraction layers such that information obtained from the devices may be provided thereto, and/or information from the other abstraction layers may be provided to the devices. In one embodiment, the various devices inclusive of the device layer 55 may incorporate a network of entities collectively known as the "internet of things" (IoT). Such a network of entities allows for intercommunication, collection, and dissemination of data to accomplish a great variety of purposes, as one of ordinary skill in the art will appreciate.

Device layer 55 as shown includes sensor 52, actuator 53, "learning" thermostat 56 with integrated processing, sensor, and networking electronics, camera 57, controllable household outlet/receptacle 58, and controllable electrical switch 59 as shown. Other possible devices may include, but are not limited to various additional sensor devices, networking devices, electronics devices (such as a remote-control device), additional actuator devices, so called "smart" appliances such as a refrigerator or washer/dryer, and a wide variety of other possible interconnected objects.

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provides cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provides pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and, in the context of the illustrated embodiments of the present invention, various workloads and functions 96 for intelligent illumination and sound control. In addition, workloads and functions 96 for intelligent illumination and sound control may include such operations as data analysis, machine learning (e.g., artificial intelligence, natural language processing, etc.), user analysis, IoT computing device characteristic parameters, as will be further described. One of ordinary skill in the art will appreciate that the workloads and functions 96 for intelligent illumination and sound control may also work in conjunction with other portions of the various abstractions layers, such as those in hardware and software 60, virtualization 70, management 80, and other workloads 90 (such as data analytics processing 94, for example) to accomplish the various purposes of the illustrated embodiments of the present invention.

Figure 4:
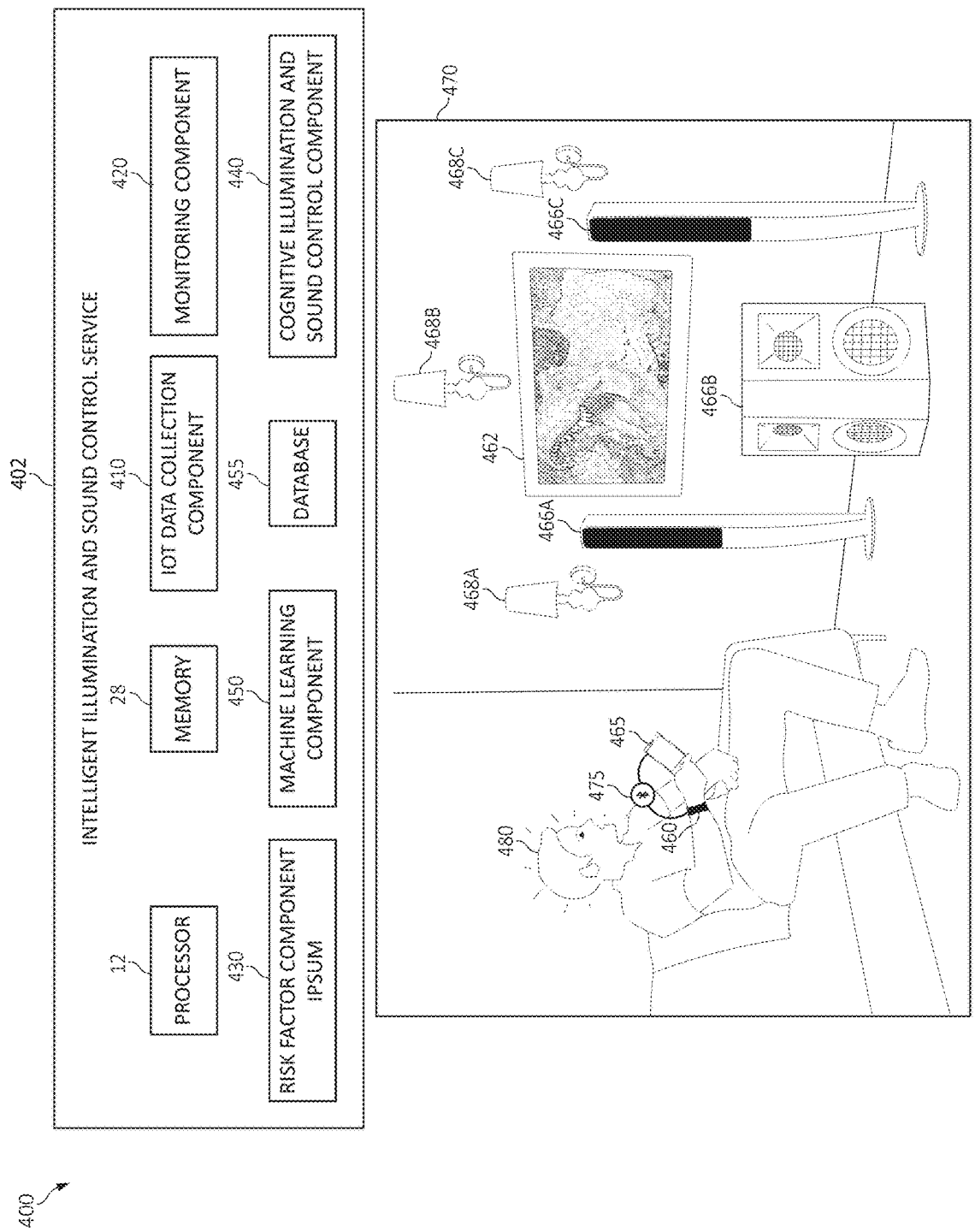
FIG. 4 is an additional block diagram depicting an exemplary functional relationship between various aspects of the present invention.

Turning now to FIG. 4, a block diagram depicting exemplary functional components 400 according to various mechanisms of the illustrated embodiments, is shown. As shown, the various functionality, or "modules" of functionality, hardware devices, and/or other components in the same descriptive sense as has been previously described in FIGS. 1-3 may be included in FIG. 4. For example, processing unit 12 and memory 28 of FIG. 1 may be employed in FIG. 4 to perform various computational, data processing, storage and other functionality in accordance with various aspects of the present invention.

The system 400 may include functional components such as an intelligent illumination and sound control service 402 (e.g., a cognitive service), having an IoT device data collection module 410, a monitoring component 420, a risk factor component 430, a cognitive illumination and sound control component 440, a machine learning module 450, a database 455, each of which may work in communication with each other.

Additionally, the intelligent illumination and sound control service 402 may perform one or more calculations according to mathematical operations or functions that may involve one or more mathematical operations (e.g., solving differential equations or partial differential equations analytically or computationally, using addition, subtraction, division, multiplication, standard deviations, means, averages, percentages, statistical modeling using statistical distributions, by finding minimums, maximums or similar thresholds for combined variables, etc.).

The intelligent illumination and sound control service 402 may be in communication with one or more IoT devices such as, for example, IoT computing device 460, 462, 465, 466A-C, and/or 468A-C. In one aspect, the IoT computing device 462 may be a media display device (e.g., a television, projection screen system, computer, laptop, and/or other devices configured to display audio and/or video data on as screen). The IoT computing device 465 may be one or more various types of communication systems (e.g., speakers, voice-activated hubs, etc.). The IoT computing devices 468A-C may be one or more illumination sources (e.g., lights, which may be external to and/or associated with IoT computing device 462). Moreover, IoT computing device 465 may be a smart phone and/or hand/held tablet. The IoT computing device 460 may be a wearable IoT device such as, for example, a smart watch.

One or more IoT computing devices such as, for example, IoT computing devices 460 and/or 465, may be used to monitor and collect a person's personal data such as, for example, data relating to one or more health state, emotional state, medical conditions, a well-being (e.g., subjective well-being "SWB", emotional well-being, mental well-being, physical well-being, or an overall well-being) of the user, an emotional state of the user, biometric data, behavior patterns, a health profile of the user, or a combination thereof. In one aspect, well-being may be generally described as a normal/standardized or satisfactory condition of existence of the user or a state characterized by health, happiness, emotional stability, mental stability, physical stability, or success. As one of ordinary skill in the art will appreciate, "well-being" may be dependent on a number of factors, including such factors as medical condition, emotional stability, mental stability, physical stability, financial stability, a degree or level of happiness, or other factors that may be learned. A well-being of a user may be defined.

The IoT computing device 460, 462, 465, 466A-C, and/or 468A-C may be devices used by cloud computers, such as, for example, the PDA or cellular telephone 54A, desktop computer 54B, laptop computer 54C, and/or automobile computer system 54N as described in FIG. 2. The IoT devices (e.g., one or more of IoT computing device 460, 462, 465, 466A-C, and/or 468A-C) may also be sensor-based devices (e.g., body mounted/implanted sensors and/or a smartwatch). The IoT computing devices 460, 462, 465, 466A-C, 468A-C may also include one or more sensors that are near a person or physically coupled to the person and are able to measure quantities that are associated with the user. For example, data relating to one or more movements of a person, physiological measurements of a person, biometric measurements used to identify a person, environmental information for the person, data from equipment held by or otherwise used by the person, or combinations thereof may be identified, collected, and/or analyzed.

The IoT device data collection module 410 may be used to harvest, collect, and store personal data in the database 455. The IoT device data collection module 410 may parse through the collected data from one or more of the IoT devices, such as IoT devices 460, 462, 465, 466A-C, and/or 468A-C (e.g., IoT device 460) which may be "wearable" devices, associated with the user to identify one or more categories that includes identifying an age of the user, medical history, medical history of one or more persons associated with the user, financial conditions, status of employment, a social media user profile, social media communication patterns, favorable and unfavorable entertainment interests, food preferences, profile types and characteristics of persons associated with the user, an emotional state of the user, biometric data, behavior patterns, or a combination thereof.

The monitoring component 420 may monitor and analyze an intensity and quality of the illumination and the sound characteristics of displayed media content in the IoT computing environment such as, for example, an entertainment system 470 (e.g., a home theater system). The monitoring component 420 may determine an interest of the one or more users in the displayed media content using one or more IoT computing devices 460, 462, 465, 466A-C, 468A-C.

The risk factor component 430 may estimate a risk factor of one or more users for both current settings and a predicted adjustment of the illumination and sound characteristics associated with displayed media content according to the analyzing. The risk factor component 430 may define the risk factor as having a potentially negative impact upon a health state, emotional state, or combination thereof of the one or more users. The risk factor component 430 may determine the risk factor according a user profile, one or more contextual factors, and one or more characteristics of the displayed media content. The risk factor component 430 may also determine and set a selected threshold for controlling the illumination, the sound characteristics, or combination thereof. For example, risk factors determined to be above the selected threshold may trigger the cognitive illumination and sound component 440 to initiate one or more corrective actions to the illumination, the sound characteristics, or combination thereof such as, for example, increasing the intensity of lighting/illumination for an age-dependent viewer having a risk factor above the selected threshold value.

The cognitive illumination and sound component 440 may control the illumination, the sound characteristics, or combination thereof of the displayed media content such as, for example, upon determining the risk factor for the one or more users is above a selected threshold. Moreover, the cognitive illumination and sound component 440 may predict the adjustment (e.g., a predicted adjustment) of the illumination and sound characteristics associated with displayed media content, or combination thereof according to one or more heuristics of the one or more users.

The cognitive illumination and sound component 440 may also implement one or more corrective actions according to monitored behavior of the one or more users, contextual factors, the risk factor, feedback data, detected patterns of discomfort to the health state, emotional state, or combination thereof of the one or more users in relation to the displayed media content.

The machine learning component 450 may initialize a machine learning operation to monitor the intensity and quality of the illumination and the sound characteristics of displayed media content, learn the risk factor for the one or more users and reaction to the displayed media content, recognize one or more illumination patterns and sounds associated with the risk factor for the one or more users, and/or collect feedback information of the one or more users relating to the displayed media content and the risk factor. Additionally, the machine learning component 450 may be initialized to learn a type of data of the user to be included in the user profile, age-dependent factors and characteristics, or a combination thereof.

The machine learning module 450 may continuously and automatically receive feedback, according to applications the illumination and sound control service 402 for each user, from one or more IoT devices, such as IoT devices 460, 462, 465, 466A-C, and/or 468A-C via a communication link 475 (e.g., wired or wireless technology including for example, but not limited to: cellular, WAN, wireless fidelity ("Wi-Fi"), Wi-Max, WLAN, Bluetooth technology, and/or combination thereof). The IoT device collection module 410 may determine whether or not each of users associated with the IoT devices 460, 462, 465, 466A-C, and/or 468A-C are reacting negatively and/or positively to both a joint analysis of both the illumination levels of one or more IoT computing devices and/or the type of content being displayed by IoT computing device 462 (e.g., a television) according to operations of the monitoring component 420.

The machine learning module 450, in conjunction with the monitoring component 420, may be used to track, monitor, and analyze feedback relating to the IoT devices, such as IoT devices 460, 462, 465, 466A-C, and/or 468A-C relating to the intelligent illumination and sound control service 402. For example, the machine learning component 450 may collect, learn, and aggregate the data of the user with collected data from one or more additional users. The machine learning component 450 may use one or more machine learning operations such as, for example, an instance of IBM® Watson® such as Watson® Analytics (IBM® and Watson® are trademarks of International Business Machines Corporation).

The IoT device collection module 410 and/or machine learning module 450 may include using one or more heuristics and machine learning based models for performing one or more of the various aspects as described herein. In one aspect, the IoT device compliance service and machine learning based models may be performed using a wide variety of methods or combinations of methods, such as supervised learning, unsupervised learning, temporal difference learning, reinforcement learning and so forth. Some non-limiting examples of supervised learning which may be used with the present technology include AODE (averaged one-dependence estimators), artificial neural network, back propagation, Bayesian statistics, naive bays classifier, Bayesian network, Bayesian knowledge base, case-based reasoning, decision trees, inductive logic programming, Gaussian process regression, gene expression programming, group method of data handling (GMDH), learning automata, learning vector quantization, minimum message length (decision trees, decision graphs, etc.), lazy learning, instance-based learning, nearest neighbor algorithm, analogical modeling, probably approximately correct (PAC) learning, ripple down rules, a knowledge acquisition methodology, symbolic machine learning algorithms, sub symbolic machine learning algorithms, support vector machines, random forests, ensembles of classifiers, bootstrap aggregating (bagging), boosting (meta-algorithm), ordinal classification, regression analysis, information fuzzy networks (IFN), statistical classification, linear classifiers, fisher's linear discriminant, logistic regression, perceptron, support vector machines, quadratic classifiers, k-nearest neighbor, hidden Markov models and boosting. Some non-limiting examples of unsupervised learning which may be used with the present technology include artificial neural network, data clustering, expectation-maximization, self-organizing map, radial basis function network, vector quantization, generative topographic map, information bottleneck method, IBSEAD (distributed autonomous entity systems based interaction), association rule learning, apriori algorithm, eclat algorithm, FP-growth algorithm, hierarchical clustering, single-linkage clustering, conceptual clustering, partitional clustering, k-means algorithm, fuzzy clustering, and reinforcement learning. Some non-limiting example of temporal difference learning may include Q-learning and learning automata. Specific details regarding any of the examples of supervised, unsupervised, temporal difference or other machine learning described in this paragraph are known and are considered to be within the scope of this disclosure. Also, when deploying one or more machine learning models, a computing device may be first tested in a controlled environment before being deployed in a public setting. Also even when deployed in a public environment (e.g., external to the controlled, testing environement), the computing devices may be monitored for compliance In view of the various components and functionality of FIG. 4, consider the following application of the present invention for predictive adjustment of illumination and sound characteristics in the entertainment system environment 470 (e.g., movie/theater setting in a home) based on contextual analysis of one or more viewers (e.g., viewer 480) and a risk analysis. In one embodiment, the present invention controls, adjusts, and/or minimizes/maximizes the illumination and sound controlling in the entertainment system environment 470 using one or more IoT devices, such as IoT devices 460, 462, 465, 466A-C, and/or 468A-C. For example, IoT device 465 may be a voice-controlled intelligent personal assistant device (e.g., a voice-activated hub) to perform joint analysis of the sound and characterize the intensity level of the sound using the monitoring component 420, which may be an illumination intensity analyzer. That is, the intensity level of the sound may be characterized by triangulating with an intensity of the illumination intensity, and the data received from other IoT devices such as, for example, IoT device 460 (e.g., a wearable device) may be analyzed. In one aspect, the joint analysis is a "conglomerate analysis" or an analysis of multiple inputs simultaneously in order to take a definite action.

By triangulating with the illumination intensity and analysis of the data received from other IoT devices 460, 462, 465, 466A-C, and/or 468A-C with respect to the one or more users such as, for example user 480, the illumination and sound control service 402 (e.g., the machine learning component 450) may learn an emotional response/stress level generated in user 480 from the displayed content, and learn the movement of the one or more users (e.g., user 480) while watching the content (e.g. a user 480 that is viewing the displayed media content while moving from room A to room B in a home or stationary, as determined by indoor position-detecting systems).

Based on the analysis of the illumination/sound and analysis of the data received from other IoT devices 460, 462, 465, 466A-C, and/or 468A-C (e.g., a wearable device), the illumination and sound control service 402 (e.g., the machine learning component 450) may be trained to recognize illumination patterns and sounds associated with risk factors for each of the one or more users (e.g., user 480) (e.g., health risk, comfort/discomfort, eye strain, fatigue, blurry vision, stress, fear, etc.), or learning to control or adjust the illumination or sound characteristics or setting. In this way, the illumination and sound control service 402 is proactive in nature by 1) reconfiguring the level and intensity of illumination in real-time such as, for example, controlling, adjusting, and/or reconfiguring a screen brightness, room brightness by activating smart light fixations for a certain duration of time, 2) personalizing the lighting/illumination or sound characteristics on the IoT devices 460, 462, 465, 466A-C, and/or 468A-C, and/or 3) personalizing the lighting and sound characteristics to assist the user in navigating through the content (e.g., user can see a summary of sections instead of watching every scene).

Also, one or more of the IoT devices such as, for example, the IoT device 465 (e.g., an illumination control device or voice-controlled intelligent personal assistant device) may store personalized illuminations or sounds for each user 480 (e.g., appropriate and acceptable illumination or sounds settings) in database 455 and communicate with a display screen of a media display device such as, for example, IoT device 462 (e.g., smart television) and/or one or more IoT devices 468A-C (e.g., "smart lights") to automatically adjust the user 480 (e.g., appropriate and acceptable illumination or sounds settings) sound to the user 480. In one aspect, a triggering operation may be initiated for controlling method based on predicated illumination or sound characteristics with respect to the risk level determine for each user (e.g., users 480).

In an additional aspect, the monitoring component 420 may monitor and analyze behavior, real-time biometric parameters (via IoT device 460 "smart watch" or other wearable sensor devices), body language, contextual factors, feedback data, detected patterns of discomfort to the health state, emotional state, or combination thereof of the user 480 with respect to the displayed video content. If the monitoring component 420 identifies that one or more viewers (e.g., users 480) having a negative emotion (e.g., fear or stress), for example, while watching the video content, the cognitive illumination and sound control component 440 associated with entertainment system environment 470 may increase the illumination level (e.g., lighting of one or more of the array of the IoT devices 468A-C and/or the IoT computing device 462 may be increased), so that the level of detected, negative emotion (e.g., fear, stress, etc.) can be minimized.

A historical medical profile (e.g. indicating a heart condition) along with real-time signals from the wearable devices (e.g., IoT device 460) of the users 480, 482 may be stored in database 455 and may be compared with an allowed/defined rate of change in biometric parameters while watching the video content.

If the rate of change in biometric parameters, for example, indicate any health-related concerns, issues, and/or problems, the intelligent illumination and sound control service 402 may be activated to control or adjust the illumination level to reduce the level of negative emotion. The intelligent illumination and sound control service 402 may identify whether the viewers of displayed video/gaming content are experiencing positive or negative emotional/behavioral responses, based on user's behavior while changing the level of illumination. The intelligent illumination and sound control service 402 may also identify and learn when to change the level of illumination with respect to the video content and viewer's real-time reaction.

In yet an additional embodiment, in the event of multi-viewer situations, if a selected number of the multiple viewers are detected as having a negative emotion while watching the video/gaming content, an appropriate illumination source from one or more of the IoT devices 468A-C may be identified to target the user 480 detected as experiencing negative emotions (e.g., higher levels of anxiety or stress compared to other users) while engaged in the contextual environment (e.g., entertainment system environment 470). For example, only a single light source 468A may be triggered to increase illumination for user 480 upon determining light source 468A is nearest to user 480.

In another embodiment, the illumination and sound characteristics can also be varied or regulated based on gaze detection and evaluation of interest of the viewers engaged in the movie or gaming environment.

In view of the various components and functionality of FIGS. 1-5, consider the following operational and implementation examples. Step 1, a camera may be installed in a home theater ecosystem to analyze body language and facial expression of one or more viewers. In step 2, one or more wearable devices may be activated to gather real time biometric parameters and to identify a rate of change in biometric parameters. In step 3, a displayed video/game from a television, along with biometric data of each viewer, may be collectively analyzed to identify the current state of the viewer (e.g., positive or negative emotion, health, and/or behavior data). The collected data may be analyzed with the video content contextually, which may be used to identify whether the change in biometric parameter and body language is aligned with the video content. Step 4, the participating viewers may also optionally provide a medical history, recent medication, and/or other health related data for analysis. The camera in an IoT and camera system can be used for identifying any recent reaction or response to the medication (e.g., identify the medication is causing the user to become drowsy, tired, weak) during a time that viewing a particular type of video/gaming content increase/decrease the health risks to the user based on the type of response to the displayed video content (e.g., becoming scared may increase adrenaline which may have a negative impact on the user in combination with the health state and/or consumed medication).

In step 5, each profile of the viewers may be analyzed and determined (e.g., fear of darkness) and identify an appropriate/minimum level of illumination required while watching any video/gaming content. In step 6, one or more viewers may be identified as having a negative emotional or behavioral response (e.g., becoming scared or afraid) while watching any video/gaming content and the exact position of the viewer may be identified to activate/create a selected amount of lighting around or near that particular viewer.

In step 7, one or more patterns of illumination may be identified and used to reduce the level of negative emotion (e.g., fear). For example, watching a movie containing sharks may cause age-dependent viewers to become afraid and put their feet down from sofa. One or more smart lights may be activated to illuminate a defined space around the sofa. Also, additional lighting in other rooms (e.g., bathroom), hallways, stairs, etc., may be proactively activated in real-time and/or upon detection/conclusion of the displayed media content to provide continual lighting and illumination as a protective measure for the age-dependent viewers.

In step 8, a machine learning operation may learn and identify a pattern of sound and associated characteristics/properties such as, for example, loudness, tonality, direction, and the like. A variation or combination of the sound characteristics may be applied and used to reduce the level of negative emotion (e.g., fear).

In step 9, the illumination may be personalized for each user such as, for example, providing personalized illumination if two or more viewers are wearing three-dimensional ("3D") goggles in a home theater. In step 10, the sound characteristics may be personalized for each user such as, for example, providing personalized sound if two or more viewers are wearing headphones in a home theater. In step 11, sound and illumination control can also be performed based on the interest of the viewers while engaged in a movie/gaming environment or a similar contextual situation. In step 12, the illumination control and contrast may be dynamically adjusted based on gaze detection and interest of plurality of viewers engaged in a gaming environment.

Figure 5:
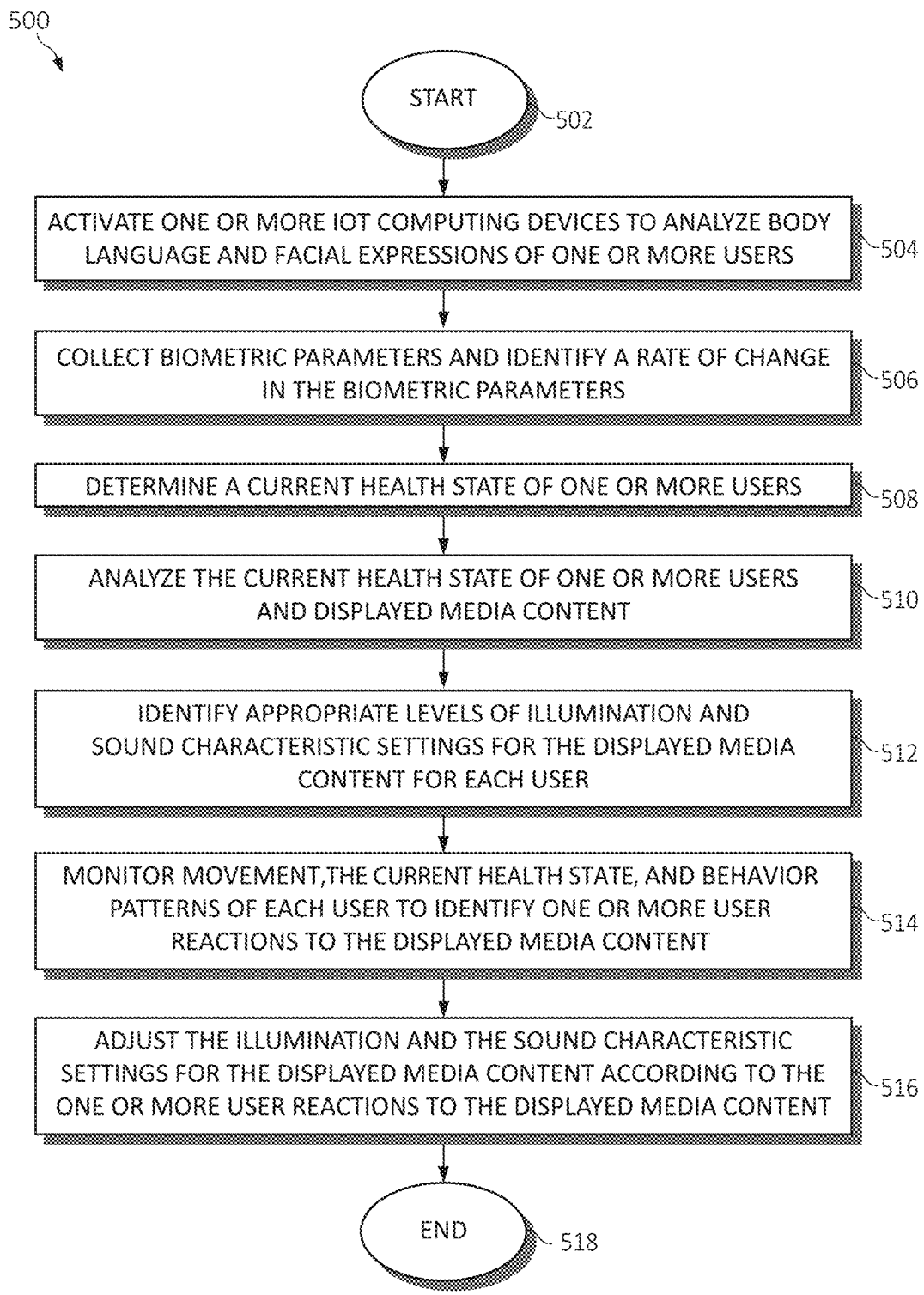
FIG. 5 is a flowchart diagram depicting an exemplary method for controlling illumination and sound characteristics of an entertainment system in an Internet of Things (IoT) computing environment in which aspects of the present invention may be realized.

Turning now to FIG. 5, a method 500 for cognitively controlling illumination and sound characteristics of an entertainment system in an Internet of Things (IoT) computing environment is depicted. The functionality 500 may be implemented as a method executed as instructions on a machine, where the instructions are included on at least one computer readable medium or on a non-transitory machine-readable storage medium. The functionality 500 may start in block 502.

One or more IoT computing devices may be activated to analyze user behavior (e.g., body language, movements, etc.) and facial expressions of one or more users, as in block 504. One or more biometric parameters may be collected and a rate of change in the biometric parameters may be identified, as in block 506. A current health state, emotional state, or combination thereof may be determined for one or more users, as in block 508. The current health state, emotional state, or combination thereof and displayed media content may be analyzed for the one or more users, as in block 510. An appropriate level of illumination and sound characteristic settings may be identified for the displayed media content for the one or more users, as in block 512. User movement, behavior patterns, and/or the current health state (including the emotional state) of the one or more users may be monitored to identify one or more user reactions to the displayed media content, as in block 514. The illumination and sound characteristic settings associated with the displayed media content may be controlled according to the one or more user reactions to the displayed media content, as in block 516. The functionality 500 may end in block 518.

Figure 6:
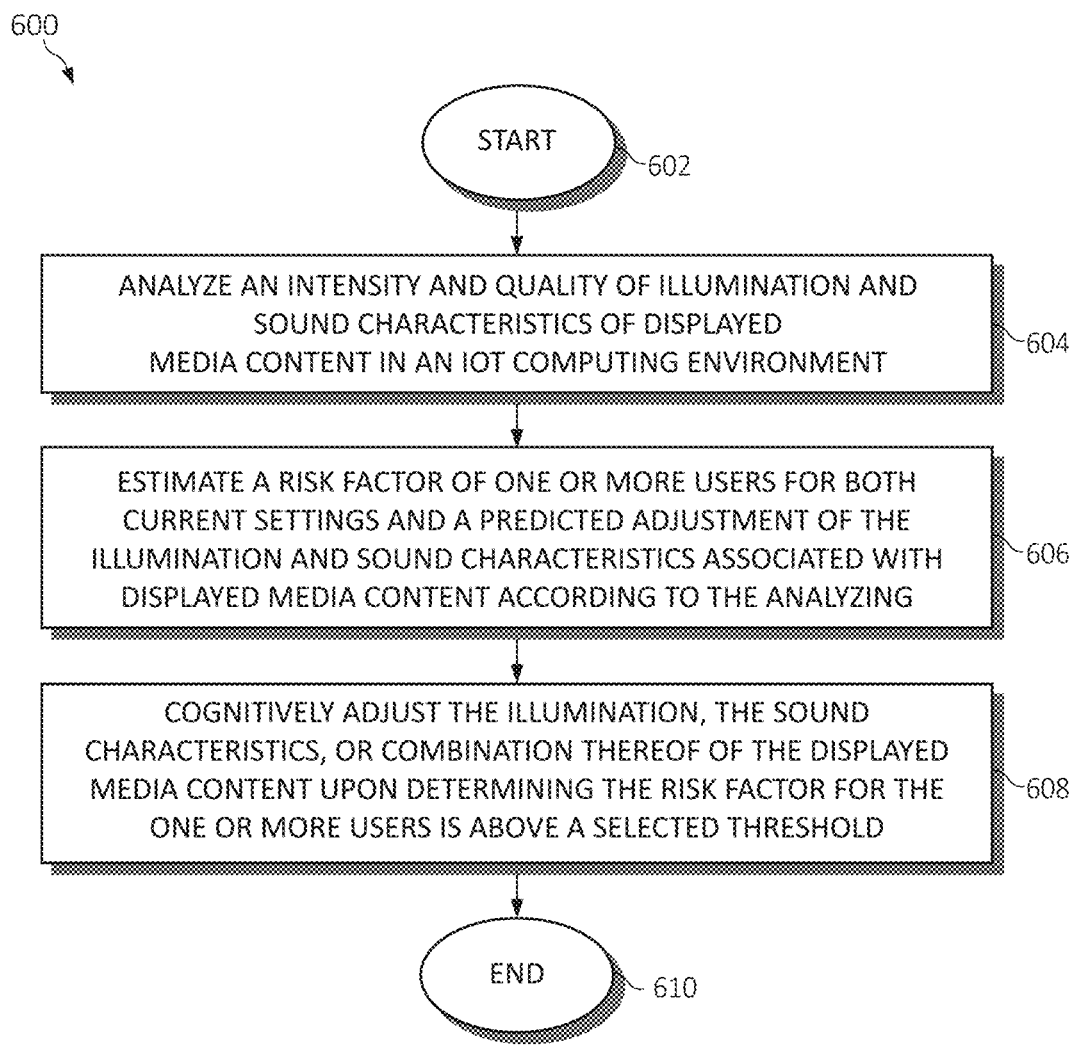
FIG. 6 is a flowchart diagram depicting an additional exemplary method for controlling illumination and sound characteristics of an entertainment system in an Internet of Things (IoT) computing environment in which aspects of the present invention may be realized.

Turning now to FIG. 6, a method 600 for cognitively controlling illumination and sound characteristics of an entertainment system in an Internet of Things (IoT) computing environment is depicted. The functionality 600 may be implemented as a method executed as instructions on a machine, where the instructions are included on at least one computer readable medium or on a non-transitory machine-readable storage medium. The functionality 600 may start in block 602.

An intensity and quality of an illumination and sound characteristics of displayed media content in an IoT computing environment may be monitored and analyzed, as in block 604. A risk factor of one or more users may be estimated for both current settings and a predicted adjustment of the illumination and sound characteristics associated with displayed media content according to the analyzing, as in block 606. The illumination, the sound characteristics, or combination thereof of the displayed media content may be adjusted upon determining the risk factor for the one or more users is above a selected threshold, as in block 608. The functionality 600 may end in block 610.

In one aspect, in conjunction with and/or as part of at least one block of FIG. 6, the operations of methods 600 may include each of the following. The operations of method 600 may initialize a machine learning operation to monitor the intensity and quality of the illumination and the sound characteristics of displayed media content, learn the risk factor for each user and reaction to the displayed media content, recognize one or more illumination patterns and sounds associated with the risk factor for the one or more users; and collect feedback information of the one or more users relating to the displayed media content and the risk factor. The risk factor may be defined as having a potentially negative impact upon a health state, emotional state, or combination thereof of the one or more users. The risk factor may be determined according a user profile, one or more contextual factors, and one or more characteristics of the displayed media content.

The operations of method 600 may predict the predicted adjustment of the illumination and sound characteristics associated with displayed media content, or combination thereof according to one or more heuristics of the one or more users. The operations of method 600 may implement one or more corrective actions according to monitored behavior of the one or more users, contextual factors, the risk factor, feedback data, detected patterns of discomfort to the health state, emotional state, or combination thereof of the one or more users in relation to the displayed media content. The operations of method 600 may also identify an interest of the one or more users in the displayed media content using one or more IoT computing device.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A method, by a processor, for implementing intelligent illumination and sound characteristics control in an Internet of Things (IoT) computing environment, comprising:
   analyzing an intensity and quality of the illumination and the sound characteristics of displayed media content in the IoT computing environment, wherein the analyzing includes analyzing both the intensity and quality of the illumination and sound characteristics of a display system rendering the media content in relation to the intensity and quality of the illumination and the sound characteristics of a room in which the display system resides;
   during with the analyzing, performing a conglomerate analysis of the illumination and sound characteristics using a first set of a plurality of IoT computing devices that analyze the intensity and quality of the illumination characteristics and a second set of the plurality of IoT computing devices that analyze the intensity and quality of the sound characteristics, wherein data produced by the first set of the plurality of IoT devices is triangulated with data produced by the second set of the plurality of IoT devices to jointly determine the intensity and qualify of the illumination and sound characteristics of the display system relative to the room in real-time;
   estimating a risk factor of one or more users for both current settings and a predicted adjustment of the illumination and sound characteristics associated with displayed media content according to the analyzing; and
   controlling the illumination, the sound characteristics, or combination thereof of the display system rendering the displayed media content and the room in which the display system resides upon determining the risk factor for the one or more users is above a selected threshold.

2. The method of claim 1, further including:
   monitoring the intensity and quality of the illumination and the sound characteristics of displayed media content;
   learning the risk factor for the one or more users and reaction to the displayed media content;
   recognizing one or more illumination patterns and sounds associated with the risk factor for the one or more users; and
   collecting feedback information of the one or more users relating to the displayed media content and the risk factor.

3. The method of claim 1, further including define the risk factor as having a potentially negative impact upon a health state, emotional state, or combination thereof of the one or more users.

4. The method of claim 1, further including determining the risk factor according a user profile, one or more contextual factors, and one or more characteristics of the displayed media content.

5. The method of claim 1, further including predicting the predicted adjustment of the illumination and sound characteristics associated with displayed media content, or combination thereof according to one or more heuristics of the one or more users.

6. The method of claim 1, further including implementing one or more corrective actions according to monitored behavior of the one or more users, contextual factors, the risk factor, feedback data, detected patterns of discomfort to the health state, emotional state, or combination thereof of the one or more users in relation to the displayed media content.

7. The method of claim 1, further including determining an interest of the one or more users in the displayed media content using one or more of the plurality of IoT computing devices.

8. A system for implementing intelligent illumination and sound characteristics control in an Internet of Things (IoT) computing environment, comprising:
   one or more computers with executable instructions that when executed cause the system to:
      analyze an intensity and quality of the illumination and the sound characteristics of displayed media content in the IoT computing environment, wherein the analyzing includes analyzing both the intensity and quality of the illumination and sound characteristics of a display system rendering the media content in relation to the intensity and quality of the illumination and the sound characteristics of a room in which the display system resides;
      during with the analyzing, perform a conglomerate analysis of the illumination and sound characteristics using a first set of a plurality of IoT computing devices that analyze the intensity and quality of the illumination characteristics and a second set of the plurality of IoT computing devices that analyze the intensity and quality of the sound characteristics, wherein data produced by the first set of the plurality of IoT devices is triangulated with data produced by the second set of the plurality of IoT devices to jointly determine the intensity and qualify of the illumination and sound characteristics of the display system relative to the room in real-time;
      estimate a risk factor of one or more users for both current settings and a predicted adjustment of the illumination and sound characteristics associated with displayed media content according to the analyzing; and
      control the illumination, the sound characteristics, or combination thereof of the display system rendering the displayed media content and the room in which the display system resides upon determining the risk factor for the one or more users is above a selected threshold.

9. The system of claim 8, wherein the executable instructions further initialize a machine learning operation to:
monitor the intensity and quality of the illumination and the sound characteristics of displayed media content;
learn the risk factor for the one or more users and reaction to the displayed media content;
recognize one or more illumination patterns and sounds associated with the risk factor for the one or more users; and
collect feedback information of the one or more users relating to the displayed media content and the risk factor.

10. The system of claim 8, wherein the executable instructions further define the risk factor as having a potentially negative impact upon a health state, emotional state, or combination thereof of the one or more users.

11. The system of claim 8, wherein the executable instructions further determine the risk factor according a user profile, one or more contextual factors, and one or more characteristics of the displayed media content.

12. The system of claim 8, wherein the executable instructions further predict the predicted adjustment of the illumination and sound characteristics associated with displayed media content, or combination thereof according to one or more heuristics of the one or more users.

13. The system of claim 8, wherein the executable instructions further implement one or more corrective actions according to monitored behavior of the one or more users, contextual factors, the risk factor, feedback data, detected patterns of discomfort to the health state, emotional state, or combination thereof of the one or more users in relation to the displayed media content.

14. The system of claim 8, wherein the executable instructions further determine an interest of the one or more users in the displayed in content one or mors of the plurality of IoT computing devices.

15. A computer program product for implementing intelligent illumination and sound characteristics control in an Internet of Things (IoT) computing environment by a processor, the computer program product comprising a non-transitory computer-readable storage medium having computer-readable program code portions stored therein, the computer-readable program code portions comprising:
an executable portion that analyzes an intensity and quality of the illumination and the sound characteristics of displayed media content in the IoT computing environment, wherein the analyzing includes analyzing both the intensity and quality of the illumination and sound characteristics of a display system rendering the media content in relation to the intensity and qualify quality of the illumination and the sound characteristics of a room in which the display system resides;
an executable portion that, during with the analyzing, performs a conglomerate analysis of the illumination and sound characteristics using a first set of a plurality of IoT computing devices that analyze the intensity and quality of the illumination characteristics and a second set of the plurality of IoT computing devices that analyze the intensity and quality of the sound characteristics, wherein data produced by the first set of the plurality of IoT devices is triangulated with data produced by the second set of the plurality of IoT devices to jointly determine the intensity and qualify of the illumination and sound characteristics of the display system relative to the room in real-time;
an executable portion that estimates a risk factor of one or more users for both current settings and a predicted adjustment of the illumination and sound characteristics associated with displayed media content according to the analyzing; and
an executable portion that control the illumination, the sound characteristics, or combination thereof of the display system rendering the displayed media content and the room in which the display system resides upon determining the risk factor for the one or more users is above a selected threshold.

16. The computer program product of claim 15, further including an executable portion that initializes a machine learning operation to:
monitor the intensity and quality of the illumination and the sound characteristics of displayed media content;
learn the risk factor for the one or more users and reaction to the displayed media content;
recognize one or more illumination patterns and sounds associated with the risk factor for the one or more users; and
collect feedback information of the one or more users relating to the displayed media content and the risk factor.

17. The computer program product of claim 15, further including an executable portion that:
defines the risk factor as having a potentially negative impact upon a health state, emotional state, or combination thereof of the one or more users; and
determines the risk factor according a user profile, one or more contextual factors, and one or more characteristics of the displayed media content.

18. The computer program product of claim 15, further including an executable portion that predicts the predicted adjustment of the illumination and sound characteristics associated with displayed media content, or combination thereof according to one or more heuristics of the one or more users.

19. The computer program product of claim 15, further including an executable portion that implements one or more corrective actions according to monitored behavior of the one or more users, contextual factors, the risk factor, feedback data, detected patterns of discomfort to the health state, emotional state, or combination thereof of the one or more users in relation to the displayed media content.

20. The computer program product of claim 15, further including an executable portion that determines an interest of the one or more users in the displayed media content using one or more of the plurality of IoT computing devices.

* * * * *